United States Patent [19]

Shibata et al.

[11] Patent Number: 4,639,305
[45] Date of Patent: Jan. 27, 1987

[54] ELECTROCHEMICAL ELEMENT
[75] Inventors: Kazuyoshi Shibata; Hitoshi Nishizawa, both of Nagoya, Japan
[73] Assignee: NGK Insulators, Ltd., Japan
[21] Appl. No.: 740,430
[22] Filed: Jun. 3, 1985
[30] Foreign Application Priority Data
  Jun. 6, 1984 [JP] Japan ................. 59-116227
[51] Int. Cl.$^4$ ........................... G01N 27/58
[52] U.S. Cl. ..................... 204/426; 204/408; 204/412; 204/424; 204/425
[58] Field of Search ............. 204/408, 412, 424, 425, 204/426, 427, 428, 429; 219/552, 553
[56] References Cited
  U.S. PATENT DOCUMENTS 4,282,080  8/1981  Muller et al. ............. 204/428 X
  4,300,990  11/1981 Maurer .................... 204/426 X
  4,334,974  6/1982  Muller et al. ............. 204/425
  4,419,213  12/1983 Oshima et al. ............ 204/426 X
  4,505,807  3/1985  Yamada ................... 204/425

Primary Examiner—John F. Niebling
Assistant Examiner—Nam X. Nguyen
Attorney, Agent, or Firm—Parkhurst & Oliff

[57] ABSTRACT

An electrochemical sensing element which includes at least one electrochemical cell having a planar solid electrolyte body and a pair of electrodes in contact with the planar solid electrolyte body, and which further includes at least one electrical heater layer which is located on one of opposite sides of the electrochemical cell. The heater layer comprises a heater member having a heat-generating portion in the form of a serpentine or sinuous strip to heat at least a portion of the electrochemical cell at which the electrodes are disposed. The serpentine strip is formed in zig-zag fashion to provide a heating region in which the heat-generating portion is accommodated. The heat-generating portion has a larger cross sectional area at its central parts located in a central portion of the heating region, than at its peripheral parts located adjacent to the periphery of the heating region.

7 Claims, 14 Drawing Figures

ELECTROCHEMICAL ELEMENT

BACKGROUND OF THE INVENTION

1. Field of the Invention

The present invention relates generally to an electrochemical element, and more particularly to an electrochemical sensing or detecting element which comprises an electrochemical cell using a planar solid electrolyte body, and an electrical heater layer disposed on one side of the electrochemical cell to form a laminar structure.

2. Related Art Statement

There have been known various electrochemical devices, each of which comprises an electrochemical element using a solid electrolyte body. Such electrochemical devices are used, for example, as oxygen sensors to detect the oxygen concentration of an exhaust gas from internal combustion engines of automotive vehicles. Typical examples of such oxygen sensors include an oxygen sensor which employs a mass of oxygen-ion conductive solid electrolyte such as a zirconia ceramic, to determine the oxygen concentration according to the principle of an oxygen concentration cell. Also known in the art are electrochemical devices or elements which are employed as sensors or detectors for hydrogen, nitrogen, carbon dioxide, etc. In recent years, there has been an increasing trend of using an electrochemical cell of laminar structure which comprises a planar solid electrolyte body and planar electrodes disposed in contact with a surface or surfaces of the planar body of solid electrolyte.

Also, it is required to provide such a laminar electrochemical cell with a suitable electrical heater for heating the electrodes and the solid electrolyte body to an elevated temperature, in order to assure accurate and reliable operation of the cell, even while the temperature of a measurement gas is relatively low. For example, it is known to form an electrical heater layer on at least one side of the planar solid electrolyte body. The heater layer includes a heater member having a heat-generating portion in the form of a serpentine or sinuous strip, which runs in meandering or zig-zag fashion to heat at least a portion of the electrochemical cell at which the electrodes are disposed.

In an electrochemical element incorporating such an electrical heater layer, however, the life of the heater member may be shortened due to overheating and consequent destruction or disconnection due to fusion of the heat-generating portion, in case where a relatively large power supply is used to energize the heat-generating portion, so as to maintain the electrochemical element at a sufficiently high operating temperature for reliable operation thereof. On the other hand, if the power supply to the heater layer is limited to an irreducible minimum to the extent necessary for maintaining the permissible lowest operating temperature of the electrochemical element or cell, the heater life may be prolonged, but there arises a problem of uneven temperature distribution at the portion of the electrochemical element which is heated by the heat-generating portion of the heater member. In this case, the insufficiently heated portion of the element is not able to perform the intended electrochemical function, which may lead to declined measuring or sensing accuracy of the electrochemical element. It is a common practice in the art that the heat-generating portion of the heater member is formed as a serpentine or sinuous strip having a constant width and a constant thickness over its entire length. In this arrangement, central parts of the heat-generating portion located in or adjacent to a central portion of a heating region accommodating the serpentine strip are less likely to dissipate heat or easy to retain or hold heat, and therefore tend to have higher temperatures, then peripheral parts of the heat-generating portion adjacent to the periphery of the heating region. Thus, it is recognized that the central parts of the heat-generating portion have a higher possibility of overheating and consequent disconnection or physical failure, than the peripheral parts.

SUMMARY OF THE INVENTION

It is therefore an object of the present invention to provide an electrochemical element including an electrochemical cell with an electrical heater layer including a heater member having a heat-generating portion in the form of a serpentine strip, wherein central parts of the heat-generating portion that are located in or adjacent to a central portion of a heating region covered or enclosed by the serpentine strip are protected from overheating and consequent disconnection, to prolong the service life of the heater layer, and wherein a portion of the electrochemical cell at which electrodes are disposed is evenly heated by the heat-generating portion of the heater member of the electrical heater layer.

According to the present invention, there is provided an electrochemical element which includes at least one electrochemical cell having a planar solid electrolyte body and a pair of electrodes held in contact with the planar solid electrolyte body, and which further includes at least one electrical heater layer located on one of opposite sides of the electrochemical cell, characterized in that the heater layer comprises a heater member having a heat-generating portion in the form of a serpentine strip to heat at least a portion of the electrochemical cell at which the pair of electrodes are disposed, the serpentine strip being formed in zig-zag fashion to provide a heating region in which the heat-generating portion is accommodated, that the heat-generating portion of the heater member has a larger cross sectional area at central parts thereof located in a central portion of the heating region, than at peripheral parts thereof located adjacent to a periphery of the heating region.

In the electrochemical element constructed as described above, the central parts of the heat-generating portion, which are located in the central portion of the heating region wherein heat is easily retained, have a larger cross sectional area than the peripheral parts, whereby the electrical resistance of the heat-generating portion or serpentine strip per unit length is smaller at its central parts than its peripheral parts. As a result, the amount of heat generated per unit area of the above-indicated heating region is smaller in the central portion than in the peripheral portion. Thus, the arrangement of the heat-generating portion according to the invention alleviates the conventional tendency of heat trapping or retention in the central portion of the heating region which is covered, enclosed or otherwise defined by the serpentine strip. This is effective in protecting the heat-generating portion or serpentine strip against overheat or disconnection due to fusion at its central parts, and permits even or uniform distribution of temperature throughout the heating region. Consequently, the corresponding portion of the electrochemical cell is evenly heated by the heat-generating portion of the heater member.

According to an advantageous embodiment of the invention, the pair of electrodes of the electrochemical cell are located inside the heating region, as seen in a plane parallel to the planar solid electrolyte body and the heater layer.

The cross sectional area of the central parts of the heat-generating portion may be made larger than that of the peripheral parts, by forming the serpentine strip such that the central parts have a larger width than the peripheral parts, while maintaining a constant thickness of the strip over its entire length. Alternatively, the serpentine strip may be formed with a constant width over its entire length, but with a larger thickness at the central parts than at the peripheral parts.

According to a preferred embodiment of the invention, the heat-generating portion of the heater member is made of a mixture of an element selected from the platinum group which comprises platinum, palladium, rhodium, iridium, ruthenium and osmium, and a ceramic material such as alumina, zirconia and yttria.

According to the invention, the aforementioned arrangement of the heater layer is advantageous, particularly when the electrochemical element comprises an electrochemical pumping cell which performs an electrochemical pumping action through an electric current flow between two pumping electrodes, and an electrochemical sensing cell which measures an electromotive force induced between a measuring electrode exposed to a measurement gas, and a reference electrode exposed to a reference gas, due to a difference in concentration of a component of the measurement and reference gases.

BRIEF DESCRIPTION OF THE DRAWING

The foregoing and other objects, features and advantages of the present invention will become obvious from the reading of the following detailed description of the illustrative embodiments, in connection with the accompanying drawings, in which.

DETAILED DESCRIPTION OF THE PREFERRED EMBODIMENTS

Referring now to the accompanying drawing, the present invention will be described in detail.

Figure 1:
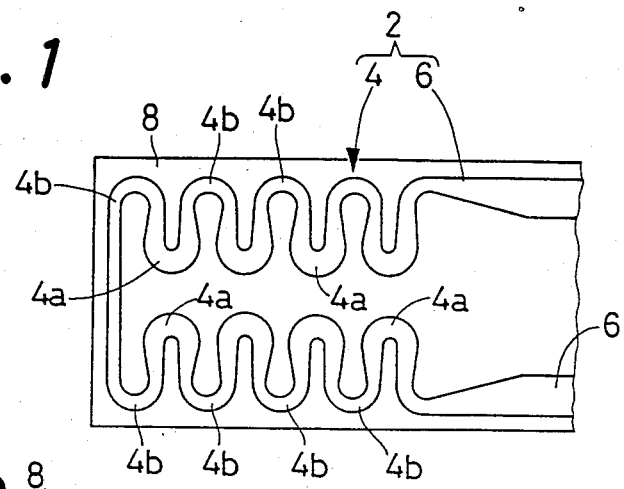
FIGS. 1, 2 and 3 are fragmentary plan views of heaters of different patterns of heat-generating portions of heater members used in an electrochemical element of the present invention.

In a plan view of FIG. 1, there is shown a portion of one example of an electrical heater layer incorporated in an electrochemical element constructed according to the invention. The heater layer comprises a heater or heater member 2 formed on a substrate 8. The heater 2 consists of a heat-generating portion 4, and a pair of leads 6, 6 for electrically connecting the heat-generating portion 4 to a suitable external power source. The heat-generating portion 4 and leads 6, 6 are formed by screen-printing, or by another suitable process known in the art.

Described more specifically, the heat-generating portion 4 and leads 6, 6 of the heater 2 are formed as an electrically conductive strip with a predetermined width. This conductive strip is made of a mixture of an element selected from the platinum group including platinum, palladium, rhodium, iridium, ruthenium and osmium, and a ceramic material such as zirconia, yttria or alumina. In order that the leads 6, 6 serve to supply power from the external power source to the heat-generating portion 4, while the heat-generating portion 4 serves to generate heat for an intended heating operation, a part of the conductive strip corresponding to the heat-generating portion 4, and parts of the strip corresponding to the leads 6, 6, are given different values of electrical resistance. Stated in more detail, the leads 6, 6 are formed to have a comparatively large cross sectional area, while the heat-generating portion 4 is formed as a conductor having a comparatively small cross sectional area. In addition, the heat-generating portion 4 and the leads 6, 6 are given different values of electrical resistance, by using the above-indicated mixture of materials of different compositions. Thus, the part of the conductive strip corresponding to the heat-generating portion 4 generates a larger amount of heat than the parts of the strip corresponding to the electrical leads 6, 6.

The inclusion of the previously indicated ceramic material in the electrically conductive metal material of the platinum group for the heater 2 improves the adhesion of the heater 2 to the substrate 8 on one side thereof, and to a ceramic layer on the other side. In forming the heater 2, fine particles of the selected ceramic material are admixed with particles of the selected metal material of the platinum group, and a paste of the mixture applied in a desired pattern is fired.

The heat-generating portion 4 of the heater 2 on the substrate 8 is provided in the form of a serpentine or sinuous strip which runs in zig-zag or meandering fashion to cover or define a heating region for efficiently heating at least a portion of the upper electrochemical cell at which electrodes are disposed. According to the invention, central parts 4a of the heat-generating portion 4 which are located in a central portion of the heating region (accommodating the pattern of the serpentine strip) are given a larger width than peripheral parts 4b of the heat-generating portion 4 located adjacent to the periphery of the heating region. However, the serpentine strip 4 is formed with a constant thickness over its entire length. Therefore, the central parts 4a have a larger cross sectional area than the peripheral parts 4b.

Accordingly, the amount of heat to be generated per unit area at the central parts 4a of the heat-generating portion 4 is made smaller than at the peripheral parts 4b, whereby the tendency of heat trapping or retention at the central parts 4a is restrained, and the heating region defined or covered by the pattern of the heat-generating portion 4 is given uniform or even temperature distribution. As a result, otherwise possible excessive temperature rise (overheat) and consequent disconnection or other destructive physical failure of the heat-generating portion 4 at its central parts 4a are effectively avoided or minimized, and the durability or service life of the heater layer is considerably improved.

Figure 2:
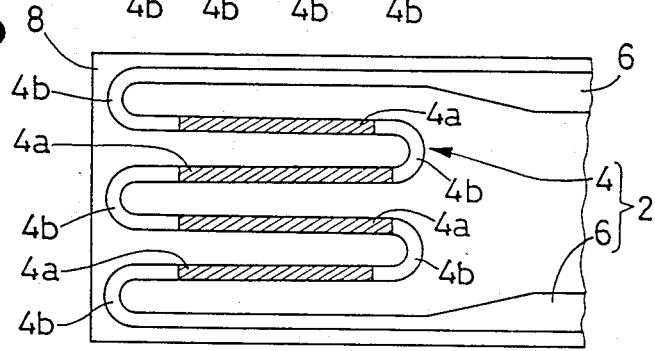

While the serpentine strip of the heat-generating portion 4 shown in FIG. 1 is formed so as to run in zig-zag fashion in opposite directions generally along the length of the substrate 8 (and along the width of the substrate 8 at its end), the serpentine strip 4 may adapted to be formed in zig-zag fashion generally in the direction of width of the substrate 8 as illustrated in FIG. 2. In this modified embodiment of the electrical heater layer, the sepentine strip 4 has a constant width over its entire length, but its thickness is made larger at the central parts 4a (hatched parts) than at the peripheral parts 4b. For example, the central parts 4a locating in a central portion of the defined heating region have a thickness of 15 microns while the peripheral parts 4b have a thickness of 10 microns. Accordingly, the cross sectional area of the central parts 4a is made larger than that of the peripheral parts 4b.

Figure 3:
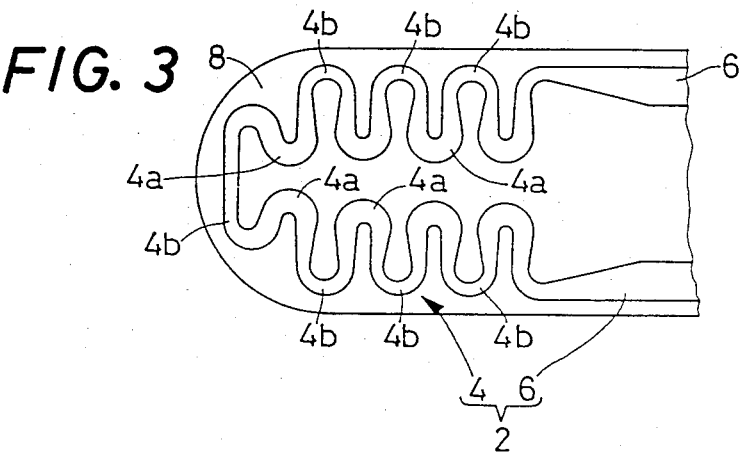

A further modified embodiment of the heater layer is shown in FIG. 3, wherein the longitudinal end portion of the substrate 8 on which the heat-generating portion 4 is disposed, is formed to have an arcuate end profile, following the configuration of the corresponding arcuate end of the electrochemical cell (not shown). Namely, one end of the electrochemical element including the electrochemical cell and the electrical heater layer with the substrate 8, is rounded to a suitable radius, so that the electrochemical cell, particularly a portion thereof at which the electrodes are located, is protected against cracking due to a rapid temperature rise by heating with the heat-generating portion 4. The substrate 8 with the arcuate end has the heat-generating portion 4 in the form of a serpentine strip which provides a heating pattern similar to that of FIG. 1, and has a larger width at its central parts 4a, than at its peripheral parts 4b.

In the illustrated examples of the electrical heater layer of FIGS. 1-3, the dimensions and location of the heating region in which the heat-generating portion 4 (serpentine strip) is formed, are adequately determined so that the heat-generating portion 4 is able to heat at least the portion of the electrochemical cell at which the electrodes are disposed. Preferably, the heating region defined by the pattern of the serpentine strip 4 is determined so that the electrodes of the electrochemical cell are located within the heating region defined or covered by the serpentine strip, as viewed in a plane parallel to the planes of the cell and heater layer. Namely, the heat-generating portion 4 is formed on the substrate 8, such that the profile of the portion 4 as viewed in a plane parallel to the surfaces of the electrodes covers the profile of the electrodes as seen in the same plane.

Figure 4A:
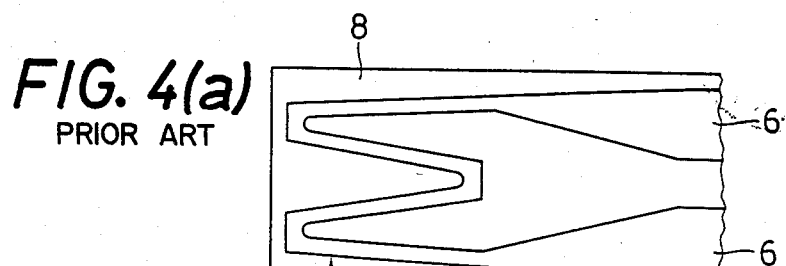
FIGS. 4(a), (b) and (c) are fragmentary plan views, similar to FIGS. 1-3, illustrating conventional heater layers.

Operating features of the electrical heater (layer) having the aforementioned heat-generating portion 4 according to the invention will become apparent from studying comparative experiments which were made on the heater of FIG. 1, and on conventional heaters with the heat-generating portions 4 illustrated in FIGS. 4(a), (b) and (c).

Figure 5A:
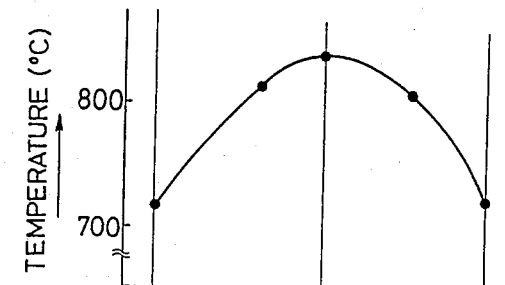
FIGS. 5(a), (b) and (c) and (d) are graphs representing curves of temperature distribution obtained on the heater members of FIGS. 4(a), (b), (c) and FIG. 1, respectively, in the direction of width of the heater layers.
Figure 5B:
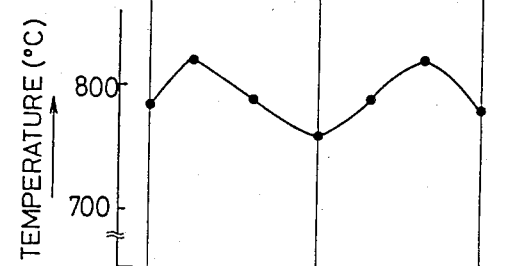
Figure 5C:
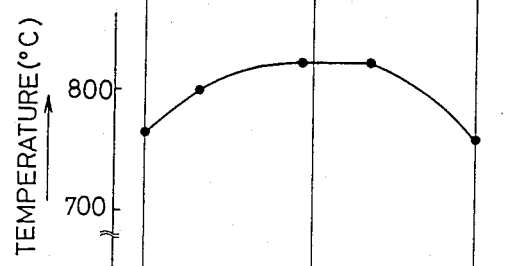
Figure 5D:
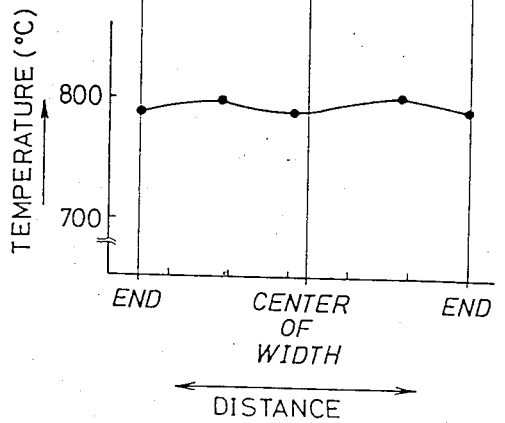

FIGS. 5(a), (b) and (c) show temperature distribution curves obtained on the conventional heaters of FIGS. 4(a), (b) and (c), respectively, while FIG. 5(d) shows a temperature distribution curve obtained on the heater of the invention illustrated in FIG. 1. The individual curves of FIGS. 5(a) through (d) represent temperatures at selected points taken across the heating region covered or defined by the respective heat-generating portions 4, in the direction of width of the heater layers. As is understood from the centrally convex or concave temperature distribution curves of FIGS. 5(a), (b) and (c), the temperatures on the conventional heaters are not evenly distributed, i.e., extremely higher or lower temperatures in the central portion of the heating region. To the contrary, the heater of the invention illustrated in FIG. 1 does not suffer an appreciable temperature variation in the direction of width of the heater layer, that is, has only a slight temperature difference within a range of 20°-30° C., which means a substantially uniform temperature distribution, as is evident from the graph of FIG. 5(d).

Figure 4B:
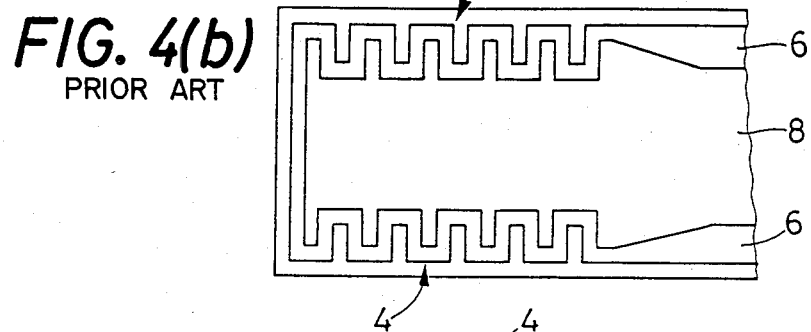
Figure 4C:
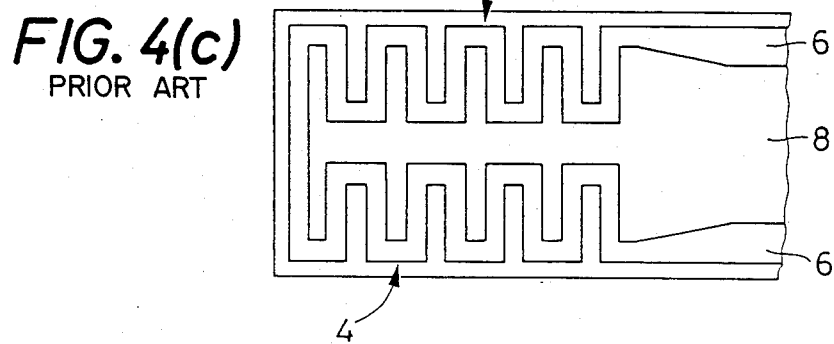

Overload tests were conducted on the instant heater of FIG. 1 and the conventional heater of FIG. 4(c), to check for durability of their heater layers. With the heat-generating portion 4 having an electrical resistance of 8.3 ohms at room temperature, an electrical power input to the heat-generating portion 4 was increased at a rate of 0.3 watt per minute, until the heat-generating portion 4 was destroyed (disconnected due to fusion). The level of the electric power upon destruction of the portion 4 was measured on three test samples for each of the heaters of FIG. 1 and FIG. 4(c). The average destructive level of the conventional heater of FIG. 4(c) was 20 watts, while that of the instant heater of FIG. 1 was 30 watts.

As indicated above, the heater of FIG. 1 provides improvements in the level of electric power input at which the heat-generating portion is deformed, fused or otherwise physically destroyed. More particularly, the heat-generating portion 4 has a reduced possibility of fusion at the central parts 4a. This reduction is attributed to the reduction in amount of heat generation per unit area at the central parts 4a, and to the uniform temperature distribution of the heat-generating portion 4.

Further tests were effected to check the instant and conventional heaters for resistance to cracking upon abrupt voltage application to the heat-generating portions 4 which have an electrical resistance of 8.3 ohms at room temperature. The cracking resistance was obtained by measuring the voltage level at which 50% of the test samples were cracked. This 50%-cracking voltage was 20 V on the conventional heater of FIG. 4(c) while that of the instant heater of FIG. 1 was 25 V. Thus, the cracking tests revealed that the heater of FIG. 1 was less subject to cracking during a rise of its temperature. This improvement in cracking resistance results from improved temperature distribution in the heating region in which the heat-generating portion 4 is formed, in particular, from enhanced distribution of temperature while the temperature rise is in progress.

Like the conventional heater, the electrical heater layer of the invention which has been illustrated is formed with respect to an electrochemical cell, such that the electrochemical cell and the heater layer constitute a desired electrochemical sensing element of a laminar structure. Examples of such a laminar electrochemical sensing element are illustrated in FIGS. 6-9.

Figure 6:
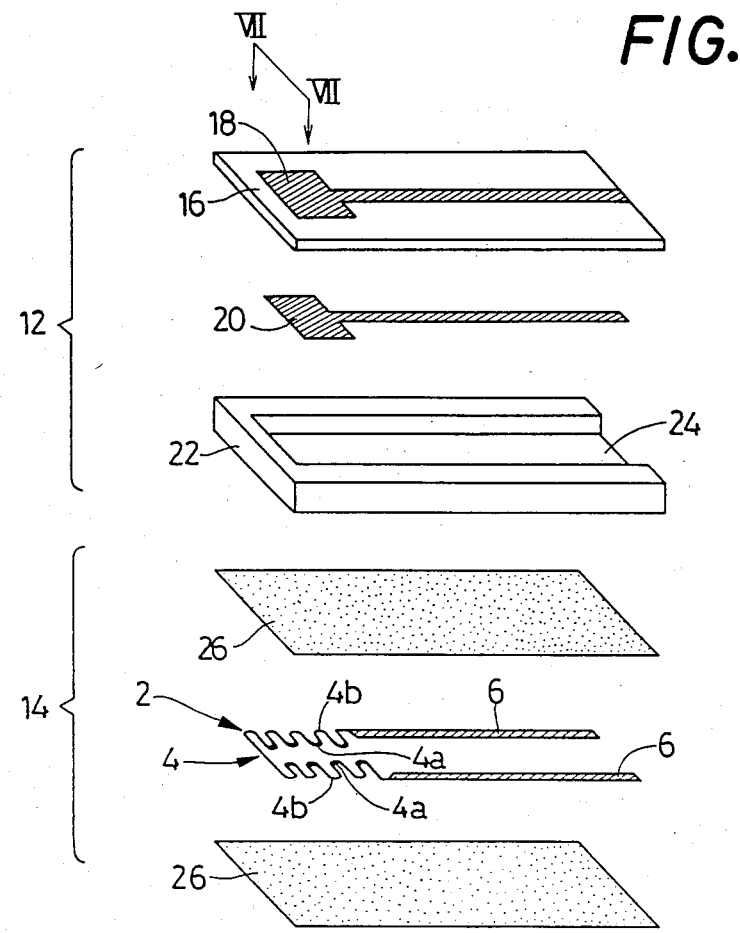
FIG. 6 is an exploded perspective view of one form of an electrochemical oxygen sensing element according to the invention.
Figure 7:
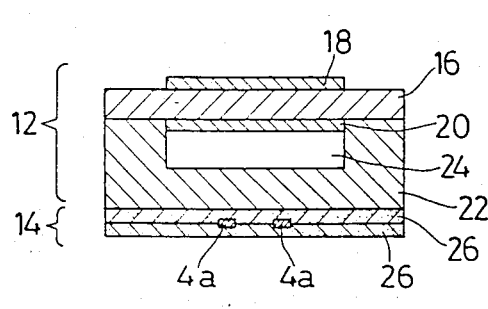
FIG. 7 is an elevational view in cross section taken along line VII—VII of FIG. 6.

Referring first to an exploded perspective view of FIG. 6, there is shown one form of an electrochemical element used as an oxygen concentration sensing element. A detecting portion of the sensing element of FIG. 6 is shown in FIG. 7 in transverse cross section, with its thickness dimension enlarged for easy understanding. The oxygen concentration sensing element (oxygen sensor) is a co-fired laminar structure which comprises a planar electrochemical cell in the form of an oxygen sensing cell 12, and a heater layer 14, which are superposed on each other.

Stated in detail, the oxygen sensing cell 12 includes a planar, gas-tight, oxygen-ion conductive solid electrolyte body 16 made, for example, of a zirconia ceramic containing yttria. On one of opposite sides of the planar solid electrolyte body 16, there is disposed a measuring electrode 18 of a porous structure made of platinum, for example. More specifically, the solid electrolyte body 16 is provided with the porous platinum measuring electrode 18 on its outer surface which is exposed to an exhaust gas or other gases to be measured. In the meantime, a reference electrode 20 is disposed on the other (inner) surface of the solid electrolyte body 16, such that the two electrodes 18 and 20 are aligned with each other. The reference electrode 20 is made of the same material as the measuring electrode 18, i.e., made of porous platinum. These two electrodes 18, 20 are connected through their leads to an external measuring apparatus (not shown) such as a potentiometer, so that an electromotive forece induced between the two electrodes 18, 20 is measured, in the same manner as practiced in a known oxygen sensor.

The reference electrode 20 is exposed to ambient air or another reference gas of a known oxygen concentration, which is introduced in a reference-gas passage 24 formed in a gas-tight spacer member 22 made of a zirconia ceramic or the like. This reference-gas passage 24 is open at one end to the ambient atmosphere, or connected at the open end to a suitable source of reference gas.

The heater layer 14 consists of a heater 2 as shown in FIG. 1, and a pair of electrically insulating layers 26, 26 made of alumina or the like. As previously described, the heater 2 includes a heat-generating portion 4 in the form of a serpentine or sinuous strip, and a pair of leads 6, 6. The serpentine strip 4 has a larger width at its central parts 4a, than at its peripheral parts 4b, so that the central parts 4a have a larger cross sectional areas than the peripheral parts 4b. The serpentine strip 4 is arranged so as to provide a heating region which covers at least a portion of the oxygen sensing cell 12 at which the measuring and reference electrodes 18, 20 are disposed. In other words, the size and location of the heating region in which the heat-generating portion 4 is formed, are selected so that at least the electrodes 18, 20 and the adjacent portion of the cell 12 may be suitably heated by the heat-generating portion 4.

In the oxygen sensing element constructed as described above, the electrodes 18 and 20 of the oxygen sensing cell 12 are evenly heated by the heat-generating portion 4 of the heater layer 14. Since the amount of heat generated per unit area is smaller at the central parts 4a than at the peripheral parts 4b, the otherwise existing tendency of higher temperature in the central portion of the heating region is effectively restrained. Hence, there are reduced chances of disconnection of the heat-generating portion 4 at its central parts, and the durability (service life) of the heater layer 14 is accordingly increased.

Figure 9:
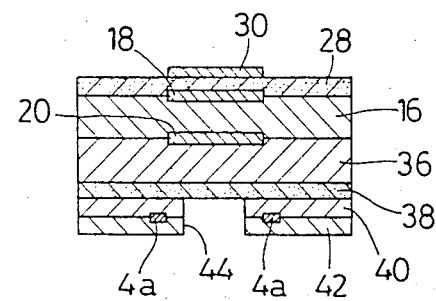
FIG. 9 is an elevational view in cross section taken along line IX—IX of FIG. 8.
Figure 8:
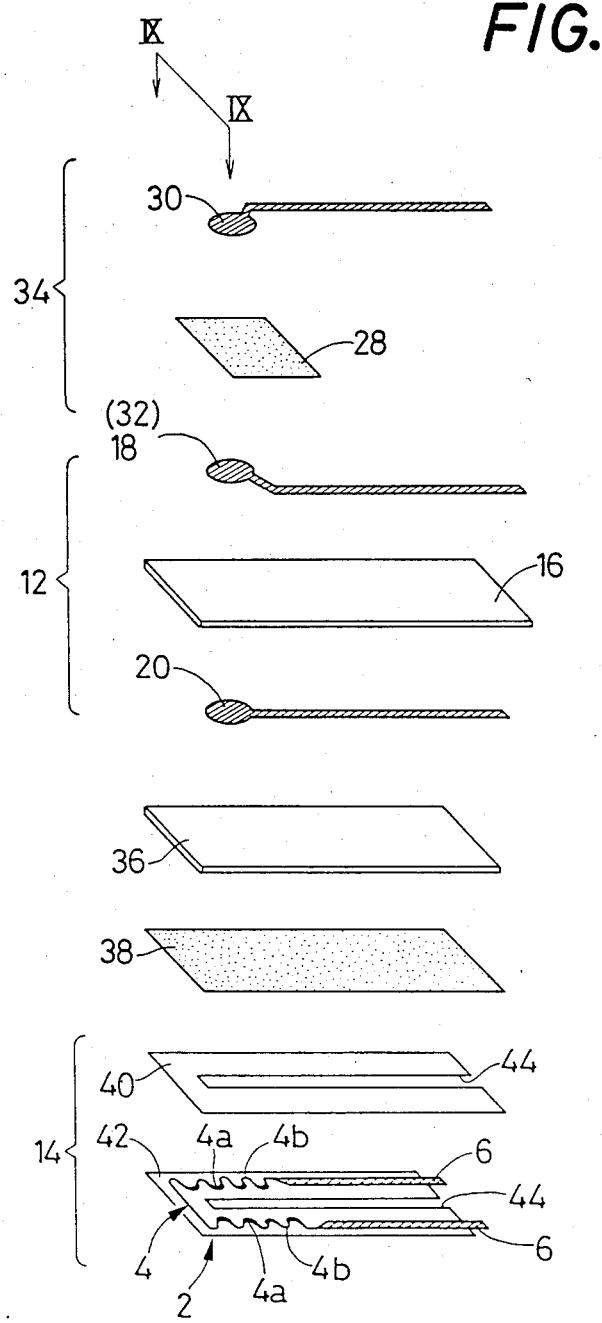
FIG. 8 is an exploded perspective view of another form of an electrochemical oxygen sensing element.

Referring next to FIGS. 8 and 9, there is shown another example of the oxygen sensing element, wherein another electrochemical cell, i.e., an oxygen pumping cell 34 is provided in addition to the oxygen sensing cell 12. The oxygen pumping cell 34 comprises a diffusion layer in the form of a planar porous solid electrolyte layer 28 made of porous zirconia ceramics, an outer pumping electrode 30 disposed on the outer surface of the planar solid electrolyte layer 28, and an inner pumping electrode 32 on the lower surface of the electrolyte layer 28. In the instant example, the measuring electrode 18 of the sensing cell 12 also serves as the inner pumping electrode 32 of the pumping cell 34.

On the surface of the planar solid electrolyte body 16 of the oxygen sensing cell 12 on which the reference electrode 20 is disposed, there is formed a gas-tight ceramic layer 36 made of a zirconia ceramic or the like, similar to the solid electrolyte body 16. An electrical heater layer 14 according to the invention is formed integrally with an laminar assembly of the oxygen pumping and sensing cells 34, 12, with an electrically insulating layer 38 of porous alumina interposed between the gas-tight ceramic layer 36 and the heater layer 14. The heater layer 14 comprises the heater 2 of FIG. 1 which is sandwiched by an upper and a lower zirconia layer 40, 42 having a high electrical resistance. A slot 44 is formed in each of the zirconia layers 40, 42, to augment electrical insulation of the heat-generating portion 4 and leads 6, 6 arranged on both sides of the slot 44.

In the aforementioned arrangement of the electrochemical oxygen sensing element, the concentration of oxygen in a measurement gas which is introduced through the porous solid electrolyte layer 28 and is brought into contact with the measuring electrode 18, is controlled by means of an electrochemical pumping action of the oxygen pumping cell 34 which is operated with an external power supply. Additionally, a current flow between the measuring and reference electrodes 18, 20 causes a suitable reference gas of a predetermined oxygen concentration to be introduced and stored in a porous structure of the reference electrode 20 which is sandwiched by the gas-tight ceramic layer 36 and the gas-tight solid electrolyte body 16. An electromotive force due to a difference in oxygen concentration is measured between the reference electrode 20 exposed to the reference gas, and the measuring electrode 18 which is exposed to the measurement gas whose oxygen concentration is controlled by the pumping cell 34 as previously described.

For reliable and accurate measurement of the electromotive force, the electrochemical oxygen sensing and pumping cells 12, 34 are heated by the heat-generating portion 4 of the heater layer 14. As previously discussed, the heat-generating portion 4 in the form of a conductive serpentine strip has a larger cross sectional area at the central parts 4a, than at the peripheral parts 4b, so that the electrical resistance per unit length of the conductive serpentine strip is smaller at the central parts 4a than at the peripheral parts 4b. Thus, the amount of heat generation per unit area at the central parts 4a is made smaller, whereby the heat-generating portion 4 is assured of even temperature distribution in the direction of width of the heater layer 14. The even temperature distribution is conductive to an improvement in the service life of the heater 2. Further, the uniform heating of the oxygen pumping cell 34, more precisely, uniform heating of the outer and inner pumping electrodes 30, 32 and the adjacent portion of the cell 34, improves the pumping characteristics of the pumping cell 34, thereby permitting precise control of the oxygen concentration of the measurement gas at the measuring electrode 18, and consequently enabling the oxygen sensing element to achieve the measurement of oxygen concentration of the measurement gas with increased accuracy. As indicated above, the heater layer according to the invention is effective and advantageous, particularly when the electrochemical sensing element includes an electrochemical pumping cell such as the pumping cell 34 which has been illustrated.

Comparative experiments were conducted on the electrochemical sensing elements of FIGS. 8-9 with the heater layer 14 using the heater 2 of FIG. 1, and on electrochemical sensing elements similar to that of FIGS. 8-9 but using conventional heater layers which include the heaters of FIGS. 4(a), (b) and (c). Table 1 shows maximum electric power input (W) and maximum temperature of the outer pumping electrode 30 at which the heat-generating portion was disconnected.

As is apparent from Table 1, the heat-generating portion 4 of the heater layer 14 of FIG. 1 of the invention had not been disconnected until the electric power input to the heater 2 was increased to as much as 30 watts. As a result, it was possible to heat the outer pumping electrode 30 of the oxygen pumping cell 34 to a comparatively far higher temperature.

TABLE 1

| Heater Layer (Heater) of | Max. Power Input (W) | Max. Temp. of Outer Pumping Electrode 30 (°C.) |
| --- | --- | --- |
| FIG. 1 | 30 | 1240 |
| FIG. 4(a) | 18 | 1060 |
| FIG. 4(b) | 21 | 1120 |
| FIG. 4(c) | 20 | 1100 |

In the electrochemical oxygen sensing element of FIGS. 8 and 9, the oxygen partial pressure (concentration) of the measurement gas to which the measuring electrode 18 of the oxygen sensing cell 12 is exposed, is also regulated by means of a diffusion resistance of the porous solid electrolyte layer 28, as well as by the electrochemical pumping action of the oxygen pumping cell 34. Hence, the oxygen partial pressure of the gas at the measuring electrode 18 may be lower than the oxygen partial pressure of the measurement gas. Accordingly, the instant oxygen sensing element is suitably used as a lean-burn sensor for controlling an engine which emits fuel-lean exhaust gases whose oxygen partial pressure is higher than that of the stoichiometric air-fuel ratio.

However, the oxygen sensing element as illustrated in FIGS. 8 and 9, which is suitably used as a lean-burn sensor, may be suitably used as oxygen sensors for detecting exhaust gases which are produced in a combustion process at substantially the stoichiometric air-fuel ratio. Further, the instant oxygen sensing element may be used as a rich-burn sensor for handling a fuel-rich exhaust gas whose oxygen partial pressure is lower than that of the stoichiometric air-fuel ratio. In any case, the concentration of oxygen (a selected component) of a measurement gas is measured in a manner known in the art.

As previously indicated, the electrical heater of the invention is advantageous, particularly when it is used for an electrochemical sensing element incorporating an electrochemical pumping cell such as the illustrated pumping cell 34, which performs an electrochemical pumping action caused by an electric current flow between the two electrodes. It will be understood that various electrochemical pumping cells are available, other than that shown in FIGS. 8 and 9, and the invention is equally applicable to those modified pumping cells. Furthermore, it will be obvious that the invention is applicable to electrochemical sensing elements as illustrated in FIGS. 6 and 7, which do not comprise an electrochemical pumping cell.

Although the present invention has been described in its preferred embodiments with a certain degree of particularity, it is to be understood that the invention is not confined to the precise disclosure contained herein, but may be otherwise embodied with various changes, modifications and improvements which may occur to those skilled in the art, in the light of the foregoing teachings, and without departing from the spirit and scope of the invention defined in the appended claims.

For example, the electrochemical element according to the invention may comprise one or two electrochemical cells, or even more than two electrochemical cells. Further, the electrical heater layer may be disposed between two electrochemical cells, rather than disposed on the outer side of an electrochemical element. Furthermore, it is possible to provide a plurality heater layers so as to sandwich an electrochemical cell or cells.

While the electrochemical element of the invention is suitably used as oxygen sensors as disclosed herein, the invention may be embodied as various other sensors or controllers for determining or regulating the concentration of specific components of a fluid associated with electrode reaction, such as nitrogen, carbon dioxide and hydrogen, other than oxygen.

As is understood from the foregoing description, the electrochemical element according to the invention is characterized by its heater layer for an electrochemical cell, wherein the heat-generating portion has a larger cross sectional area at its central parts located in a central portion of a heating region covered by the heat-generating portion, than at its peripheral parts located adjacent to the periphery of the heating region, thereby providing even or uniform temperature distribution in the heating region, and consequently improving the durability of the heater. Thus, the invention has an important industrial significance.

What is claimed is:

1. An electrochemical element comprising:
   at least one electrochemical cell having a planar solid electrolyte body and a pair of electrodes held in contact with said planar solid electrolyte body;
   at least one electrical heater layer which is located on one of opposite sides of the electrochemical cell, said heater layer comprising a heater member having a heat-generating portion shaped in a serpentine strip to heat at least a portion of said electrochemical cell at which said pair of electrodes are disposed, said serpentine strip being formed in a zig-zag fashion to provide a heating region in which said heat-generating portion is accommodated;
   said heat-generating portion having a cross sectional area at central portions thereof located in a central portion of said heating region, which is greater than a cross sectional area at a peripheral portions thereof located adjacent to a peripheral portion of said heating region, such that said heat-generating portion provides a substantially uniform distribution of temperature throughout the heating region.

2. An electrochemical element as recited in calim 1, wherein said pair of electrodes are located inside said heating region, with respect to a plane parallel to said planar solid electrolyte body and said heater layer.

3. An electrochemical element as recited in claim 1, wherein said serpentine strip has a constant thickness over its entire length, and a larger width at said central portion thereof, than at said peripheral portions thereof.

4. An electrochemical element as recited in claim 1, wherein said serpentine strip has a constant width over its entire length, and a larger thickness at said central portion thereof than at said peripheral portions thereof.

5. An electrochemical element as recited in claim 1, wherein said electrical heater layer further comprises a substrate having an longitudinal end portion upon which said serpentine strip is formed, said longitudinal end portion including an arcuate end.

6. An electrochemical element as recited in claim 1, wherein said heat-generating portion comprises a mixture of an element of a platinum group and a ceramic material.

7. An electrochemical element as recited in claim 1, wherein said at least one electrochemical cell comprises an electrochemical pumping cell which performs an electrochemical pumping action through a flow of current between two pumping electrodes, and an electrochemical sensing cell which measures an electromotive force induced between a measuring electrode exposed to a measurement gas, and a reference electrode exposed to a reference gas, due to a difference in concentration of a component of the measurement and reference gases.

* * * * *